United States Patent [19]
Barlow et al.

[11] Patent Number: 5,466,371
[45] Date of Patent: Nov. 14, 1995

[54] CYTOCENTRIFUGATION DEVICE

[75] Inventors: Wayne K. Barlow, Providence; Carmelo G. Quirante, Logan, both of Utah

[73] Assignee: Wescor, Inc., Logan, Utah

[21] Appl. No.: 134,083

[22] Filed: Oct. 8, 1993

Related U.S. Application Data

[63] Continuation-in-part of Ser. No. 788,310, Nov. 5, 1991, Pat. No. 5,252,228.

[51] Int. Cl.$^6$ .............................................. B04B 5/02
[52] U.S. Cl. .................... 210/361; 422/72; 422/101; 494/16; 494/36
[58] Field of Search ................ 210/361; 422/72, 422/101; 494/16, 45, 36

[56] References Cited

U.S. PATENT DOCUMENTS

| | | | |
|---|---|---|---|
| 4,853,188 | 8/1989 | Toya | 210/361 |
| 5,252,228 | 10/1993 | Stokes et al. | 210/781 |

OTHER PUBLICATIONS

P. Watson, A slide centrifuge, Journal of Laboratory Clinical Medicine 1966, vol. 68, pp. 494–501.

Primary Examiner—Matthew O. Savage
Attorney, Agent, or Firm—Mallinckrodt & Mallinckrodt

[57] ABSTRACT

A cytocentrifugation device of the type disclosed by the copending Stokes-Quirante U.S. application Ser. No. 07/788,310 (U.S. Pat. No. 5,252,228 on Oct. 12, 1993) is improved by the provision of elongate, rounded projections on and protruding from the clamping face of the delivery conduit flange at the delivery end of such conduit and the flattening of the otherwise rounded and flange contacting end faces of the clamping arms. Further improvements include a floating mounting for the clamping arms so as to ensure even clamping of the annular area of the absorption pad marginal to the absorption pad opening confronting the cell deposition area of the microscope slide that is otherwise covered by the absorption pad, and the provision for positively, properly aligning the several items to be clamped together during operation of the cytocentrifuge apparatus.

21 Claims, 3 Drawing Sheets

CYTOCENTRIFUGATION DEVICE

Prior Application

This application is a continuation-in-part of application Ser. No. 07/788,310, now U.S. Pat. No. 5,252,228, filed Nov. 5, 1991, of Barry O. Stokes and the present joint applicant, Carmelo G. Quirante, entitled "Improved Cytocentrifugation Device, Apparatus and Method", hereinafter referred to as "the Wescor apparatus and device."

BACKGROUND OF THE INVENTION

1. Field

The invention is in the field of cytocentrifugation devices as used in cytocentrifugation apparatus and is particularly concerned with improvements to the cytocentrifugation device disclosed in the aforesaid copending application Ser. No. 07/788,310 assigned to Wescor, Inc., Logan, Utah, now U.S. Pat. No. 5,252,228 on Oct. 12, 1993.

2. State of the Art

The apparatus and device of the aforementioned Stokes and Quirante patent application (the Wescor apparatus and device) are improvements on the apparatus and device of the Alan J. Gordon U.S. Pat. No. 4,391,710 of Jul. 5, 1983 that is assigned to Shandon Southern Products Limited, Runcorn, England. In the patented Shandon apparatus (the Shandon "Cytospin"), multiple cytocentrifugation devices for holding a cell-containing sample liquid and flowing it onto a microscope slide for the deposit on such slide of cells contained by the sample liquid are individually removably mounted in a rotary carrier (rotor) of the apparatus. The cell-containing sample liquid flows along a sample retention chamber of tubular formation under the influence of centrifugal force to an absorption pad confronting a face of a microscope slide held by a slide holder portion of the device. Such slide holder is provided with clamping means for holding together the flanged discharge end of the sample retention tube, the absorption pad, and the microscope slide during operation of the centrifuge. The cell-containing liquid is introduced into the sample retention tube through a funnel formation at the feed end of such tube and all parts of each device, including the slide holder and clamping means, are removable as a unit from the rotary carrier or rotor of the apparatus.

The improvements made to the Shandon "Cytospin" apparatus and device by the Wescor apparatus and device developed prior to the present invention were directed toward achieving retention of a greater number of cells on the deposition face of the slide than had been possible theretofore, and included the positive retention of the cell-containing sample liquid in a sample chamber that feeds into a flow conduit extending between such chamber and the slide holder. Such slide holder incorporates the clamping means and is non-removably secured to the rotary carrier or rotor of the apparatus for the purpose of greater security in use of the apparatus.

One aspect of the Wescor device constituting an improvement on the Shandon "Cytospin" device was the provision of at least two chambers in line along a liquid delivery conduit that corresponds to the Shandon sample retention tube, except for being fed during centrifugation with an absorption-pad-wetting liquid from the one chamber that is forwardly located and therefore closer in line to the delivery end of the sample delivery conduit than is the chamber containing the sample liquid so that the absorption-pad-wetting liquid positively reaches the absorption pad in advance of the cell-containing sample liquid. At least a third chamber for containing a cell-fixative solution is preferably provided, being in line rearwardly of the sample chamber so as to positively deliver fixative solution to the cell-receiving face of the slide after deposition of the cells thereon.

A second aspect of the Wescor device is the provision of an absorption pad that is formed with a relatively thin marginal area surrounding the usual hole through which the sample liquid reaches the deposit face of the slide and with a relatively thick surrounding area for absorption and retention of the sample liquid after cells have been deposited on the deposit face of the slide within the area of such usual hole through the absorption pad. This, of course, is useful whether or not there are multiple in-line chambers according to the first aspect of such Wescor improvements.

A further aspect of the Wescor improved device, that may be utilized whether or not the foregoing aspects are employed, is the novel construction of the clamping means relative to the holder for the microscope slide and for the absorption pad.

SUMMARY OF THE INVENTION

The present improvements on the Wescor device are concerned with the microscope slide and absorption pad holder and with the clamping means in order to positively achieve substantially uniform clamping pressure throughout substantially the entire marginal area of the absorption pad surrounding the usual hole through such absorption pad confronting the area of the microscope slide on which the cells are to be deposited.

An important feature of the invention is the arrangement of the clamping arms so as to float and self-align horizontally relative to the pivot shaft on which they are mounted.

Another feature is the provision of elongate, outward protrusions on the pressure-receiving face of the usual flange surrounding the delivery end of the liquid delivery conduit, such protrusions being rounded and extending laterally from such conduit delivery end, centered with respect to the delivery conduit, and the flattening of such protrusion-contacting face portions of the otherwise rounded ends of the clamping arms.

Still another feature is the provision of oppositely arranged sets of mating alignment members on absorption pad holder, absorption pad, and the sample liquid flow conduit flange to insure proper alignment of these structures for clamping together relative to the microscope slide on which cells are to be deposited.

THE DRAWINGS

The best mode presently contemplated for carrying out the invention in actual practice is illustrated in the accompanying drawings, in which:

FIG. 1 is a fragmentary top plan view of the Wescor cytocentrifugation apparatus showing a single device portion of the rotor as broken out from such rotor, the improved device shown constituting a preferred embodiment of the present invention;

FIG. 2, a vertical section taken along the line 2—2 of FIG. 1 but with a portion of the side of the frame being broken away to show the absorption pad in section;

FIG. 3, a transverse vertical section taken along the line 3—3 of FIG. 1;

FIG. 4, a fragmentary horizontal section taken along the line 4—4 of FIG. 3 and drawn to a larger scale;

FIG. 5, a transverse vertical section taken along the line 5—5 of FIG. 2 and drawn to a larger scale to show details of the floating mounting for the clamping arms;

FIG. 6, an exploded perspective view of the slide and absorption pad holder with a slide in place;

FIG. 7, a top plan view similar to FIG. 1, but showing an alternative spring arrangement; and FIG. 8, a transverse vertical section similar to that of FIG. 3, but showing the spring arrangement of FIG. 7.

DETAILED DESCRIPTION OF THE ILLUSTRATED EMBODIMENT

Figure 1:
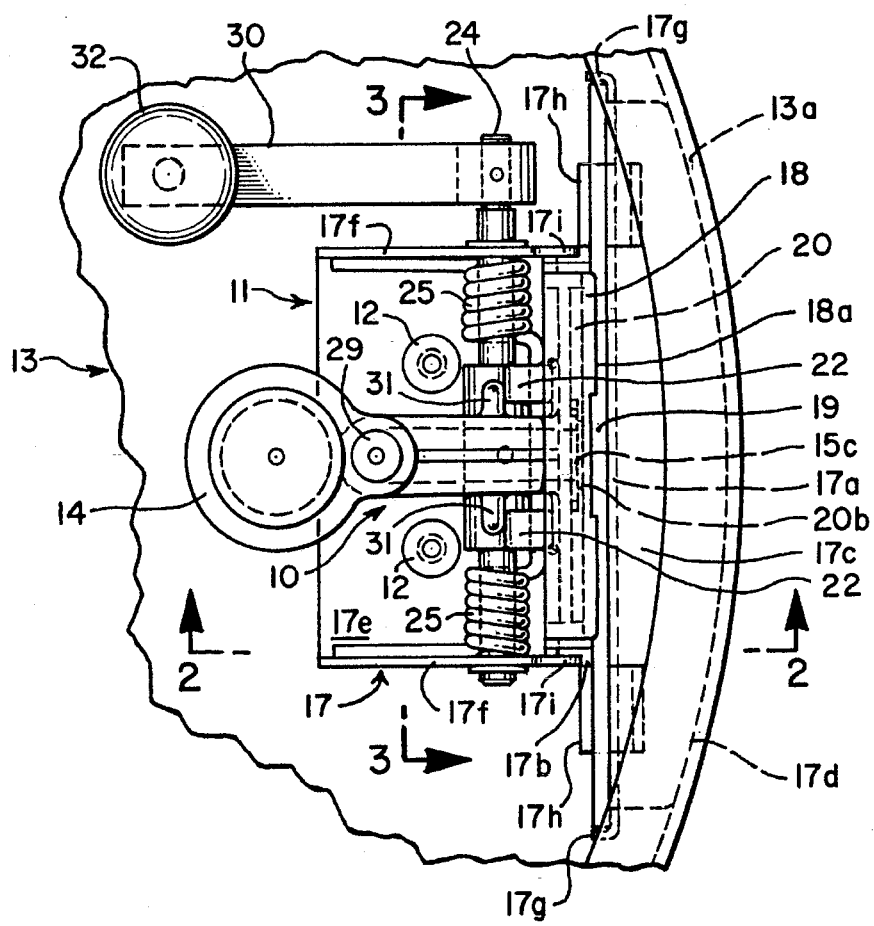

The preferred form of the present invention as applied to the Wescor cytocentrifugation apparatus and device illustrated and described in the afore-referred-to copending Stokes and Quirante application Ser. No. 07/788,310 (incorporated herein by reference) is illustrated in the several figures of the accompanying drawings in which most of the reference numbers do not correspond with those used in said application.

Thus, a cytocentrifugation device 10 is removably inserted into receiving clamping means 11, which is non-removably secured, as by screws 12, to a circumferential portion of a rotor or rotary carrier 13 of the cytocentrifugation apparatus.

In the device 10, a chamber 14 for a cell-containing sample liquid communicates, through a lateral opening 14a, with the feed end 15a of a delivery conduit 15 whose discharge end 15b surrounding and defining discharge opening 15c terminates beyond a rectangular flange 16 extending substantially perpendicularly to conduit 15, hereinafter referred to as an outward flange.

Rotor 13 has an outer, circumferential wall 13a against which the device 10 is positioned through the intermediacy of the clamping means 11, which clamping means comprises a transversely extending fixture 17 having an upstanding, rectilinear, transverse, rear wall member 17a, which is stepped at 17b intermediate its length for receiving and supporting the discharge end 15b of delivery conduit 15 and which has a rearwardly extending, horizontal wall member 17c terminating in an arcuate, rear edge 17d curved to fit against the inner face of carrier wall 13a.

Fixture 17 has a base web member 17e extending between a pair of upstanding, side wall members 17f, respectively, which, as shown, are spaced somewhat forwardly from rear wall member 17a and rise above the stepped portion 17b thereof. Screws 12 pass through web member 17e and secure fixture 17 more or less permanently to the floor of rotor 13. A slide 19 is received in fixture 17 against upstanding rear wall member 17a and between its, forwardly extending lateral wall ends 17g, FIG. 1, and is supported by respective slide bottom supporting ears 17h, FIG. 2.

Figures 4, 5:
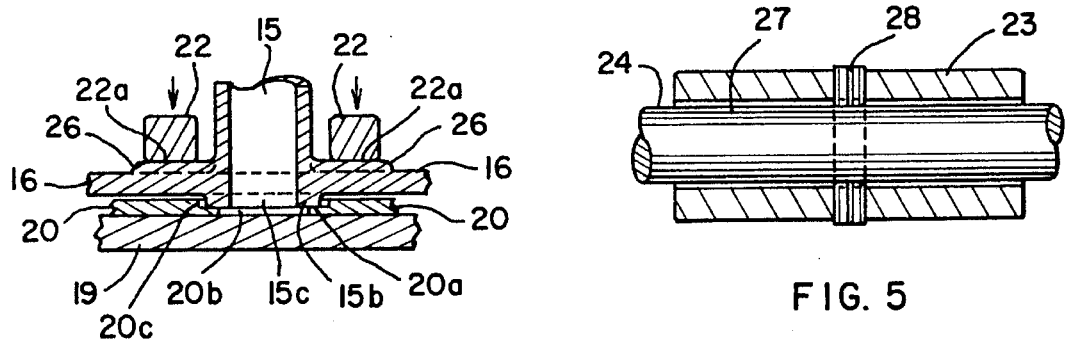

The stepped portion 17b of fixture rear wall member 17a serves to receive and support an absorption pad holder 18 with received absorption pad 20. Absorption pad 20, when arranged in normal operating position as shown, see particularly FIGS. 2 and 4, confronts the forward face of slide 19 and lies between it and the annular discharge end 15b of flow conduit 15, with such discharge end 15b fitted against the depressed, relatively thin, portion 20a of absorption pad 20 marginal to an absorption pad opening 20b that is opposite, i.e., aligned with or concentric with, discharge opening 15c. In operation of the cytocentrifugation apparatus, a cell-containing sample liquid flows from chamber 14 through conduit 15, out conduit discharge opening 15c, through absorption pad opening or hole 20b and onto the forward face of microscope slide 19. Although hole 20b may be of the same size as conduit discharge opening 15c, i.e., commensurate in shape and size therewith, or even smaller than discharge opening 15c, it is presently preferred that hole 20b be slightly larger than conduit discharge opening 15c to allow more cells in the sample liquid to reach the slide before the carrying liquid is absorbed into the absorption pad around hole 20b. It has been found that making the hole 20b about 0.06 inches larger in diameter than conduit 15 gives good results.

In the form illustrated, holder 18 is a rectangular, open frame, having opposite end walls narrower than opposite longitudinal walls so as to provide a longitudinal slideway 18a at its rear face for accommodating a microscope slide 19. The absorption pad 20 conforms in shape and size with the inside of holder frame 18 and is pushed into place internally of such frame from its front face thereof so the depression 20c, FIG. 6, leading to the precompressed, relatively thin and annular, marginal portion 20a thereof faces forwardly. Finally, the delivery end 15b of conduit 15 of cytocentrifuge device 10, with its rectangular flange 16, is pushed into the front-open face of holder frame 18 so that such conduit discharge end 15b is inserted into the depression 20c and bears against portion 20a of absorption pad 20 that is marginal to opening 20b through such absorbent pad. Slide bottom support ears 17h are slightly higher than stepped portion 17b so that the bottom of a slide 19 is supported above the lower slideway portion 18a, FIGS. 2 and 6, of the lower longitudinal wall of holder 18. This ensures that when device 10 with holder 18 thereon is placed in fixture 17 and holder 18 rests on stepped portion 17b, slide 19 fits into slideway 18a of holder 18 and confronts absorption pad 20. Holder 18 serves as an alignment means to align the absorption pad 20 so that hole 20b is aligned with conduit discharge end 15b.

With the absorption pad 20 as shown, the pad should be inserted into holder 18 so that depression 20c faces forwardly. For insuring proper orientation of the absorption pad within frame 18, such frame is provided internally with oppositely arranged alignment members, preferably in the form of elongate tongues 21, see particularly FIG. 6, parallel with the longitudinal axis of conduit 15 and adapted to receive correspondingly placed, mating grooves 20d, respectively, formed in the longitudinal edge margins of absorption pad 20, and to receive correspondingly placed, mating grooves 16a, respectively, formed in the longitudinal edge margins of conduit flange 16. Such tongues 21 extend perpendicularly from slideway 18a across the respective widths of the longitudinal walls of frame 18, i.e. transversely of holder 18 and of the held absorption pad, and are secured longitudinally thereof to the holder, being positioned so that absorption pad 20 can be inserted only with the desired orientation.

Figure 3:
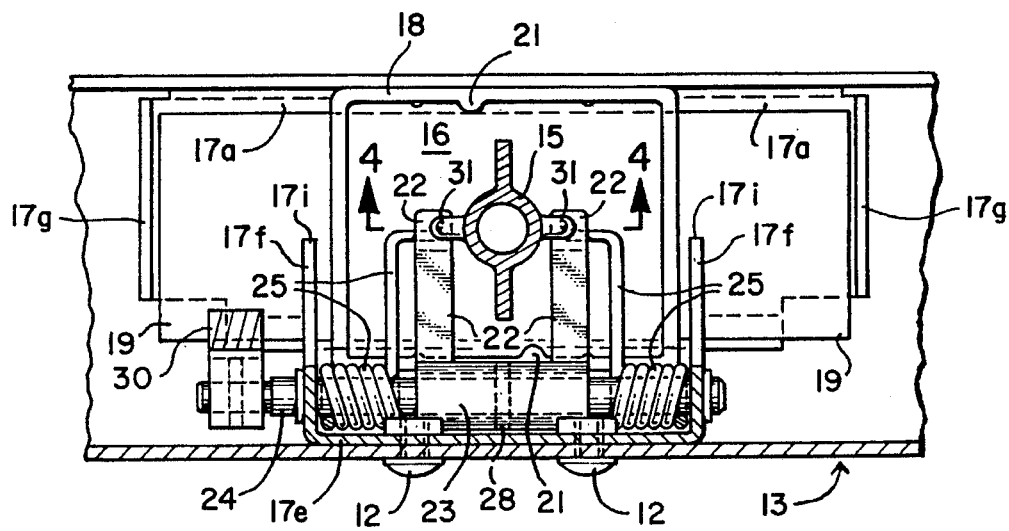

The clamping means 11 is similar in most respects to that of the prior Wescor device, having a pair of spring-biased, clamping arms 22 extending rigidly from securement to opposite ends, respectively of a sleeve member 23, FIG. 3 rotatably mounted on a pivot shaft 24 which extends transversely of fixture 17 with its ends journaled in sidewall members 17f of such fixture. A pair of coil springs 25, respectively, are carried on pivot shaft 24 between corresponding arms 22 and side wall members 17f, with opposite ends of such springs being anchored in fixture web member 17e and in receiving holes, respectively, in the ends of arms 22.

In the prior Wescor device, the rectangular flange of the cytocentrifuge device is flat and the ends of the clamping arms where they contact the flange are rounded. It has been found that for best deposition of cells onto a slide, it is important that substantially uniform pressure be applied completely around the marginal area 20a of the absorption pad surrounding the hole 20b. Pressure applied to rectangular flange 16 is applied to such marginal area 20a by discharge end 15b of flow conduit 15 which extends rearwardly of flange 16 to contact marginal area 20a. When the ends of the clamping arms are rounded and the surface of the flange contacted by the clamping arms is flat, the relative positioning of the clamping arms and flange are critical to applying substantially uniform pressure through the flow conduit end to the absorption pad. To apply the desired uniform pressure, the ends of the respective clamping arms should contact the surface of the flange on opposite sides of the flow conduit along extensions of a diameter through the flow conduit, i.e., a line drawn between the contact points on opposite sides of the conduit should pass through the center or longitudinal axis of the conduit. This will be referred to as "centered" with respect to the conduit. It has been found that if the contact points are displaced from such a line, i.e., the line between the contact points is displaced from the center of the conduit, more than about 0.01 inch, the force transmitted to the absorption pad is off center with respect to the discharge end of the conduit, resulting in uneven pressure being applied to the pad by the discharge end of the conduit around the hole. This uneven pressure allows uneven fluid flow out of the side of the hole having a lesser amount of pressure applied thereto and, as the pressure becomes more uneven, such uneven flow increases and as it becomes more rapid causes cells to be swept from the slide into the pad with the rapid fluid flow.

Figure 2:
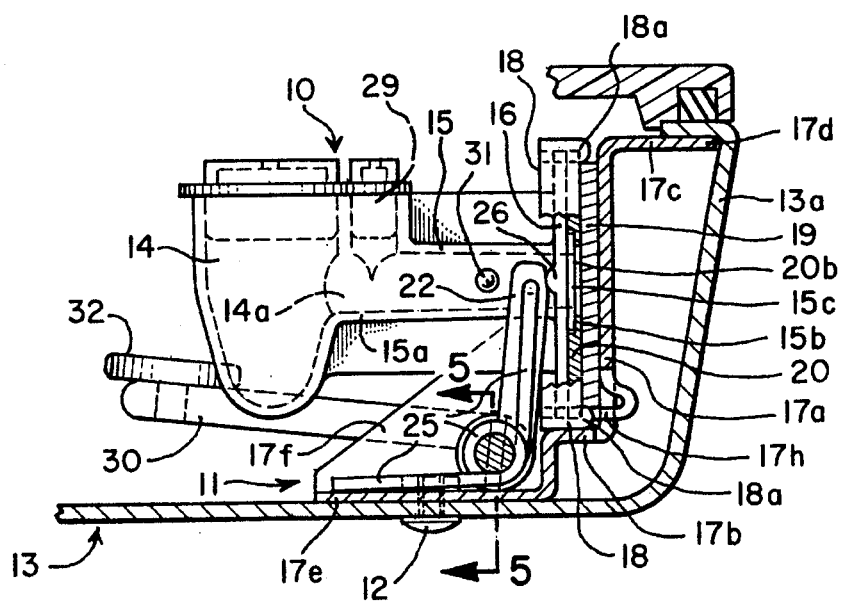
Figure 6:
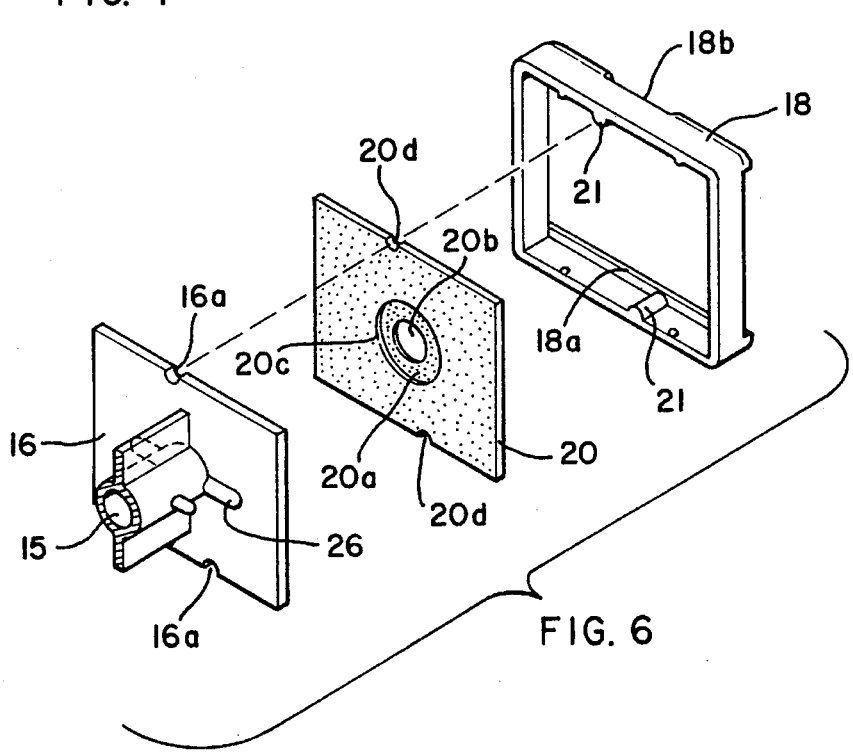

In accordance with the present invention, a pair of elongate, longitudinally rounded protuberances 26, respectively, FIGS. 2 and 6, are formed on the forward surface of conduit flange 16 and are secured thereto and project therefrom along their lengths, extending laterally from conduit 15 and centered with respect to conduit 15 for the application of clamping pressure thereto by the free terminal ends 22a of clamping arms 22, which terminal ends are flattened rearwardly, as illustrated, for directly confronting such protuberances 26. With the terminal end portions of the clamping arms 22 flat, and the protuberances rounded, the arms will always contact and transmit the clamping pressure to the highest edge of the rounded protuberances 26. With the protuberances aligned with conduit 15, pressure applied to the protuberances is automatically centered with respect to conduit 15 and the discharge end 15b thereof to provide substantially uniform pressure to the marginal area 20a of absorption pad 20 around hole 20b. Thus, the positioning of the clamping arms 22 with respect to the flange 16 is not critical since, as long as the clamping arms contact the top of the protuberances, the force transmitted by the clamping arms to the discharge end of the conduit will be centered.

A further consideration in centering the force applied by clamping arms 22 is to ensure that the force applied by each of the arms is substantially equal. The rigid securement of clamping arms 22 to sleeve member 23 tends to ensure this equal force, but tolerances in forming the flat faces on the arms and fabricating the holder assembly and possible flexibility of the arms may cause some unevenness. Thus, further in accordance with the present invention, clamping arms 22 and sleeve member 23 to which they are rigidly attached, as by being formed integrally therewith, and from which they extend are mounted on pivot shaft 24 so as to float thereon and thereby be able to compensate for any irregularities that would otherwise tend to cause application of non-uniform pressure by such clamping arms 22. For this purpose, a clearance 27, FIG. 5, of typically seventeen thousandths of an inch is provided between the outer circumferential surface of pivot shaft 24 and the inner circumferential surface of clamping arm sleeve 23. A pivot pin 28 passing transversely through sleeve 23 and into a receiving opening in shaft 24 secures sleeve 23 to shaft 24 intermediate the clamping arms 22 and serves as a pivot shaft about which the sleeve can pivot to provide the floating action of sleeve 23 and the clamping arms 22. To allow the desired float or equalization, it should be noted that pin 28 is substantially aligned in parallel with the longitudinal axes of the clamping arms.

It should be realized that, while a second chamber 29 is shown in line with sample liquid receiving chamber 14 leading into the feed end of delivery conduit 15, as in the aforesaid Wescor device, only the single chamber 14 need be provided so far as the present invention is concerned if so desired.

After cytocentrifugation is completed, the slide 19 upon which cells have been deposited, and the device 10 with holder 18 and pad 20 thereon, are separated and removed separately from the apparatus. As in the prior Wescor device, a lever arm 30 is affixed to a protruding end of pivot shaft 24 as a manually manipulatable handle for retracting the device 10 with frame 18 and absorption pad 20 relative to clamping fixture 17 against the urge of springs 25 by exerting backward pressure on retraction pins 31 projecting outwardly of conduit 15 in the line of backward travel of clamping arms 22. Slide 19 is held against movement by upstanding ends 17i of walls 17f. As thereby separated from slide 19, device 10 with holder frame 18 and pad 20 can be easily removed from the apparatus. Thereafter, slide 19, with its deposit of cells in the circular area comprehended by delivery opening 15c of conduit 15, can be easily removed from fixture 17. The order of removal indicated, i.e., device 10 with holder 18 and pad 20 thereon first, followed by slide 19, is presently preferred, removal in reverse order, i.e., slide 19 first, is also satisfactory. In the event holder 18 scrapes against slide 19 during removal of device 10 or slide 19, the deposited cells on slide 19 are protected from being inadvertently scraped from the slide by reason of correspondingly placed indentations 18b, FIG. 6, in the longitudinal walls defining slideway 18a. After removal of device 10 with holder 18 and pad 20 thereon, holder 18 can be removed from flange 16 and the spent absorption pad 20 may be removed and thrown away before replacement by a fresh absorption pad. As illustrated, it is desirable that a push tab 32 be provided at the free end of lever arm 30.

Absorption pad 20 is preferably pre-formed with depression 20c for receiving the delivery end 15b of conduit 15 and with the relatively thin annular portion 20 marginal to opening 20a precompressed to a desired extent for limiting the rate of lateral flow of liquid from absorption pad opening 20b. It has been found that the clamping pressure applied by means of the spring-biased, floating clamping arms 22, along with the extent of precompression of the portion 20a of the absorption pad, controls the rate of absorption of liquid from opening 20b into absorption pad 20.

While the two spring arrangement illustrated in FIGS. 1–3 and as used in the prior Wescor device, with the improvements described here, works well when the two springs are substantially balanced, it is presently contemplated that use of a single spring will eliminate the need to balance the two springs and will simplify assembly. Such an arrangement is shown in FIGS. 7 and 8 wherein a single spring is used.

Figure 7:
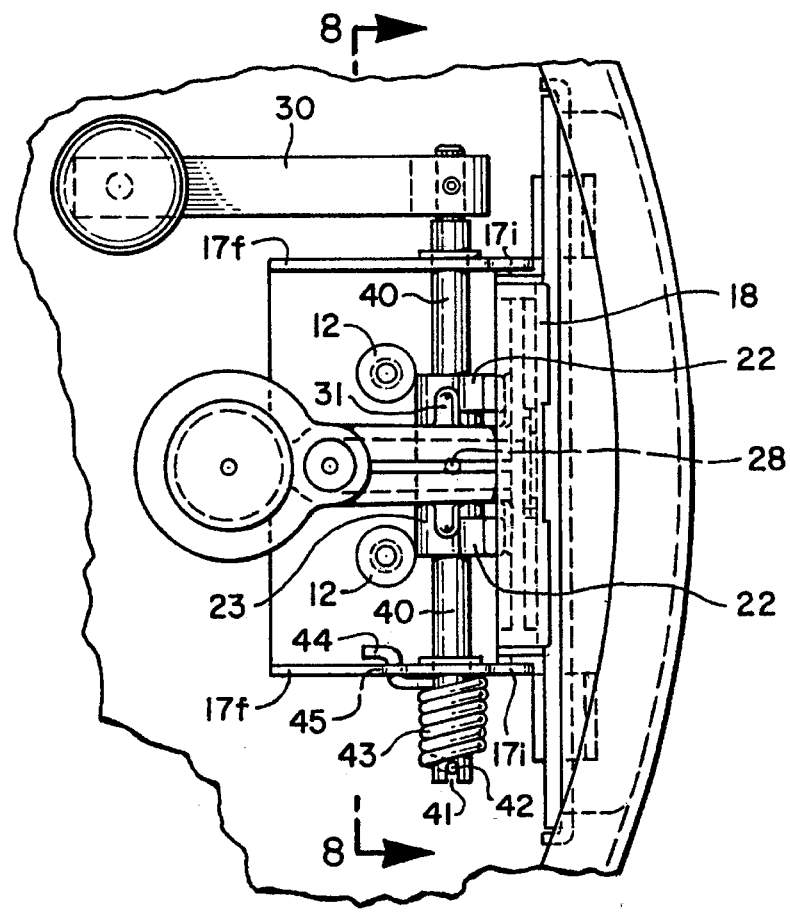
Figure 8:
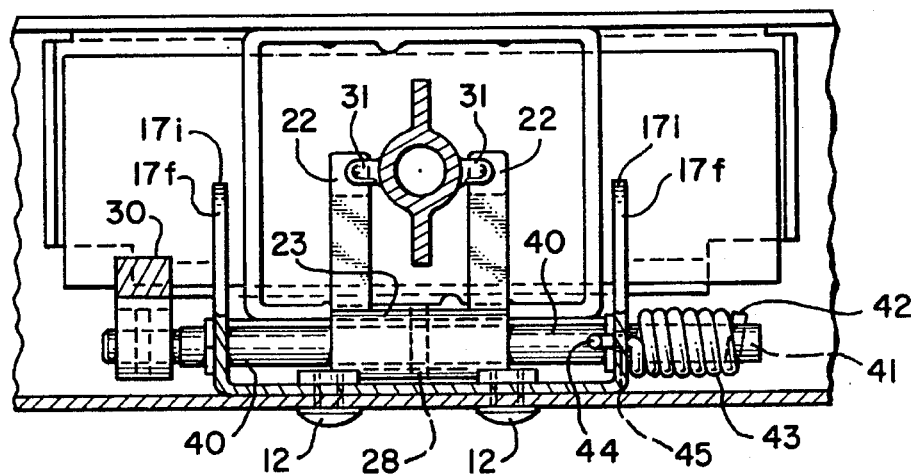

With the arrangement of FIGS. 7 and 8, pivot shaft 40, which corresponds to pivot shaft 24 of FIGS. 1–5, has its end opposite lever arm 30 extended beyond side wall 17f. A slot 41 in the end of extended shaft 40 receives the end 42 of a coil spring 43, with the other end of coil spring 43 configured as at 44 to be received and held by opening 45 in adjacent wall 17f. Spring 43 is provided as a torsion spring, and is preloaded during assembly on shaft 40 so that in the configuration shown, it will urge shaft 40 to rotate to urge clamping arms 22 against flange 16. Pivot pin 28 transmits the rotational force of shaft 40 to sleeve 23 and clamping arms 22. Sleeve 23 is preferably arranged to float on shaft 40 about pivot pin 28 as previously described.

While it is presently preferred to use all of the improvements described herein together, it should be realized that any one of the improvements can be used alone in connection with cytocentrifugation apparatus to improve performance. Also, while use of the orientation alignment means described is presently preferred so that the absorption pad has to be inserted with depression 20c facing discharge end 15b, it is contemplated that absorption pads may be configured so that orientation is not important. In such case, the alignment members or tongues will not be necessary as the alignment between the absorption pad and the conduit discharge end is determined by the frame 18 which receives the absorption pad and the conduit flange 16. Further, while it is presently preferred to use the frame 18 for holding and aligning the conduit flange, absorption pad, and microscope slide, the frame could be eliminated and the absorption pad otherwise positioned between the conduit discharge end and the slide.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. For use in cytocentrifugation apparatus, a cytocentrifugation device comprising: a conduit having a central axis and an outwardly flanged discharge end defining a discharge opening for delivering a cell-containing sample liquid to the confronting face of a microscope slide, the flange of said outwardly flanged discharge end having a clamping face directed oppositely of said discharge opening; an elongate holder for an absorption pad extending transversely across said discharge end of said conduit so that a hole through the absorption pad received by said holder will be aligned with said discharge opening, said holder being adapted to receive said flanged discharge end of said conduit so as to confront a filter pad received by said holder; and oppositely arranged sets of mating alignment members on said flanged discharge end of said conduit and on said holder, respectively, for positively insuring proper alignment of said conduit, of said holder, and of an absorption pad held by said holder and provided with cooperative mating alignment members, when said conduit, said holder, and said absorption pad are clamped together with a microscope slide within cytocentrifugation apparatus, said sets of mating alignment members each comprising an elongate tongue secured to said holder internally thereof and having a major axis extending parallel to the central axis of said conduit; and a correspondingly oriented, tongue-receiving groove formed in an edge margin of the flange of the flanged discharge end of the conduit.

2. A cytocentrifugation device according to claim 1, including an absorption pad within the holder and having a set of correspondingly oppositely arranged tongue-receiving grooves formed in edge margins thereof.

3. A cytocentrifugation device according to claim 1, wherein the holder is provided with a slideway for a microscope slide.

4. A cytocentrifugation device according to claim 1, including elongate, longitudinally rounded protuberances secured along their lengths to and projecting outwardly of the clamping face of the flange of the flanged discharge end of the conduit and transversely of the conduit at opposite lateral sides, respectively, thereof for clamping contact by clamping means wherein said protuberances extend along a transverse axis that is substantially perpendicular to the central axis of said conduit, and wherein each said protuberance includes an elongate rounded surface portion that extends substantially symmetrically about and is substantially parallel to said transverse axis.

5. For use in cytocentrifugation apparatus, a cytocentrifugation device comprising: a conduit having a central axis and an outwardly flanged discharge end defining a discharge opening for delivering a cell-containing sample liquid to the confronting face of a microscope slide, the flange of said outwardly flanged discharge end having a clamping face directed oppositely of said discharge opening; alignment means for aligning an absorption pad having a hole therethrough so that said hole is aligned with said discharge opening and for holding alignment while said flange and an absorption pad are clamped together with a microscope slide within cytocentrifugation apparatus; elongate, longitudinally rounded protuberances secured along their lengths to and projecting outwardly of said clamping face of the flange of the flanged discharge end of the conduit at opposite lateral sides, respectively, of said conduit for clamping contact by clamping means wherein said protuberances extend along a transverse axis that is substantially perpendicular to the central axis of said conduit, and wherein each said protuberance includes an elongate rounded surface portion that extends substantially symmetrically about and is substantially parallel to said transverse axis; and clamping means having elongate clamping arms pivotally mounted and spring biased and with flat clamping faces at the ends thereof confronting the rounded protuberances, respectively, for normally exerting clamping pressure thereon.

6. The combination recited in claim 5, wherein the pivotal mounting of the clamping arms comprises a sleeve to which said arms are rigidly secured and from which they rigidly extend; a pivot shaft on which said sleeve is mounted longitudinally thereabout, there being clearance between said sleeve and shaft so said arms float relative to said shaft; and means pivotally securing said sleeve to said shaft extending transversely thereof and located intermediate of said arms for permitting said sleeve to pivot about an axis that is substantially parallel to a longitudinal axis of said clamping arms.

7. The combination recited in claim 6, wherein the clamping means further comprises a clamping fixture within which the pivot shaft is journaled and provided with means for securement to the rotor of cytocentrifugation apparatus.

8. The combination recited in claim 7, wherein the clamping fixture has a base web arranged for securement to the rotor of cytocentrifugation apparatus and having upstanding side walls and opposite ends, respectively, of said web, opposite ends of the pivot shaft being journaled in said side walls, respectively; a stepped, upstanding wall rising from securement to said web and spaced, above its stepped formation, from said side walls to provide for the reception of the holder of the cytocentrifugation device and for support thereof on said stepped formation; coil spring means mounted on said pivot shaft for urging the clamping arms against the rounded protuberances; and a lever arm secured to said pivot shaft providing a manually manipulatable handle for turning said pivot shaft and the sleeve with its clamping arms against the clamping urge of said spring means.

9. The combination of claim 6, wherein the means pivotally securing the sleeve to the shaft is a pivot pin that is substantially aligned in parallel with the longitudinal axes of the clamping arms.

10. A cytocentrifugation device according to claim 5, wherein the rounded protuberances extend laterally along a line extending through the center of the conduit.

11. For use in cytocentrifugation apparatus, a cytocentrifugation device comprising: a conduit having a central axis and an outwardly flanged discharge end defining a discharge opening for delivering a cell-containing sample liquid to the confronting face of a microscope slide, said flanged discharge end being adapted to confront an absorption pad extending transversely across said discharge end of said conduit so that a hole through the absorption pad is aligned with said discharge opening, the flange of said flanged discharge end having a clamping face directed oppositely of said discharge opening; and elongate, longitudinally rounded protuberances secured along their lengths to and projecting outwardly from said clamping face of said flange and extending transversely of said conduit at opposite lateral sides, respectively, thereof for clamping contact by clamping means wherein said protuberances extend along a transverse axis that is substantially perpendicular to the central axis of said conduit, and wherein each said protuberance includes an elongate rounded surface portion that extends substantially symmetrically about and is substantially parallel to said transverse axis.

12. The device of claim 1 and clamping means having clamping arms pivotally mounted and spring biased and with flat clamping faces at the ends thereof confronting the rounded protuberances, respectively, for normally exerting clamping pressure thereon.

13. The device of claim 12, wherein the protuberances and the clamping arms consist of pairs thereof, respectively.

14. The device of claim 11, wherein the rounded protuberances extend laterally along a line extending through the center of the conduit.

15. The device of claim 11, wherein a holder is provided for an absorption pad to be confronted by the conduit flange, said holder extending transversely across the discharge end of the conduit and being adapted to receive the flanged discharge end of the conduit so as to confront an absorption pad received by the holder and to position the discharge end of the conduit and the absorption pad so that a hole through the absorption pad is aligned with said discharge opening.

16. The device of claim 11, additionally including an absorption pad extending transversely across the discharge end of the conduit, said absorption pad being located so that a hole therethrough is aligned with the discharge opening of the conduit when said pad is confronted in operating position by the conduit flange.

17. For use in cytocentrifugation apparatus, a cytocentrifugation device comprising: a conduit having an outwardly flanged discharge end defining a discharge opening for delivering a cell-containing sample liquid to the confronting face of a microscope slide, said flange adapted to confront an absorption pad extending transversely across said discharge end of said conduit so that a hole through the absorption pad is aligned with said discharge opening, the flange of said flanged discharge end having a clamping face directed oppositely of said discharge opening; clamping means for retaining said device within the rotor of cytocentrifugation apparatus, said clamping means comprising clamping arms confronting said clamping face of said flange and pivotally mounted by means of a sleeve to which they are rigidly secured and from which they rigidly extend; a pivot shaft on which said sleeve is mounted longitudinally thereabout, there being clearance between said sleeve and shaft so said arms float relative to the cytocentrifugation device; and means pivotally securing said sleeve to said shaft extending transversely of said shaft and located intermediate of said arms for permitting said sleeve to pivot about an axis that is substantially parallel to a longitudinal axis of said clamping arms.

18. The device of claim 17, wherein a holder is provided for an absorption pad to be confronted by the conduit flange, said holder extending transversely across the discharge end of the conduit and being adapted to receive the flanged discharge end of the conduit so as to confront an absorption pad received by the holder and to position the discharge end of the conduit and the absorption pad so that a hole through the absorption pad is aligned with said discharge opening.

19. The device of claim 17, including spring means operative upon the pivot shaft to urge the clamping arms toward and against the flanged discharge end of the conduit.

20. The device of claim 19, wherein the spring means comprises a pair of springs mounted on the pivot shaft at opposite ends of the sleeve, respectively.

21. The device of claim 19, wherein the spring means comprises a single spring mounted on an end portion of the pivot shaft.

* * * * *